US006161941A

United States Patent [19]
Tait et al.

[11] Patent Number: 6,161,941
[45] Date of Patent: Dec. 19, 2000

[54] LIGHT ARRAY SYSTEM AND METHOD FOR ILLUMINATION OF OBJECTS IMAGED BY IMAGING SYSTEMS

[75] Inventors: Robert W. Tait, Brighton, Mich.; Alvaro D. Lewin, Austin; Mark R. DeYong, Round Rock, both of Tex.

[73] Assignee: Intelligent Reasoning Systems, Inc., Austin, Tex.

[21] Appl. No.: 09/139,172

[22] Filed: Aug. 24, 1998

[51] Int. Cl.[7] .................................................. F21V 21/00
[52] U.S. Cl. ...................... 362/249; 362/283; 362/347; 362/350; 362/800
[58] Field of Search .................................... 362/249, 252, 362/282, 283, 800, 347, 350, 235

[56] References Cited

U.S. PATENT DOCUMENTS

| | | | |
|---|---|---|---|
| 4,774,643 | 9/1988 | McGinnis et al. | 362/189 |
| 5,038,258 | 8/1991 | Koch et al. | 362/237 |
| 5,039,868 | 8/1991 | Kobayashi et al. | 250/572 |
| 5,309,277 | 5/1994 | Deck | 359/387 |
| 5,920,643 | 7/1999 | White et al. | 382/141 |

*Primary Examiner*—Alan Cariaso
*Assistant Examiner*—John Anthony Ward
*Attorney, Agent, or Firm*—Gray Cary Ware & Freidenrich LLP

[57] ABSTRACT

An illumination system and method for providing wide angle illumination to objects to be inspected. The illumination system includes a dome light array having a plurality of rows where each row includes a plurality of lamps arranged in an arc about an imaging area (so that each lamp in the row is approximately the same distance from the imaging area) and all of the lamps in a row point to and illuminate the same point within the image area. The illumination system can include an aperture in the top of the dome light array through which a camera can image the object. Positioning each row of lamps in an arc about the image point provides various illumination angles to give a relatively uniform wide angle, yet intense, illumination to enhance automated PWB defect inspection. To further provide illumination, a pair of side panel light arrays having a plurality of lamps can be attached to the sides of the dome light array so that the side lamps provide further vertical illumination on the image area from a horizontal side plane.

40 Claims, 6 Drawing Sheets

LIGHT ARRAY SYSTEM AND METHOD FOR ILLUMINATION OF OBJECTS IMAGED BY IMAGING SYSTEMS

TECHNICAL FIELD OF THE INVENTION

The present invention relates generally to illumination systems and methods, and more particularly, to a light array system and method for illumination of objects for machine vision, inspection, and image processing applications, and even more particularly to a light array system and method for illumination of objects to be inspected using one dimensional imaging systems.

BACKGROUND OF THE INVENTION

Inspection of manufactured products helps to reduce the number of defective products introduced into the marketplace. The effectiveness of certain types of inspections, for example inspections of printed circuit boards or printed wiring boards (collectively "PWBs"), is often dependent upon the illumination systems and processes used to provide inspection lighting of the manufactured product during inspection.

This is especially true for automated inspection of PWBs using line scan cameras—the ability to identify, classify, and properly detect defects in the inspected PWBs is greatly affected by the lighting available on the subject PWB. Proper illumination allows for enhanced visibility of PWB manufacturing defects, including raw paste analysis (coverage and volume, missing/mis-aligned/damaged components, bent/missing/lifted leads, bridges and near bridges, alignment gauging, insufficient and excess solder, solder dewets, cold and fractured solder joints, etc.).

Several different illumination methodologies have been used for PWB inspection as well as other inspection tasks. These illumination techniques include highly diffuse ("cloudy day") illumination, direct illumination, re-directed illumination using fiber optics to distribute the source over a line, projected images of lines, ring lights, coaxial illumination, flood lights, as well as all of the above with some form of additional diffuser. Each of these methods proves inadequate when used for automated inspection of PWBs using a line scan camera for at least one or more of the following reasons: (1) inadequate overall light level; (2) excessive localized blooming or glinting (i.e., saturation of camera imaging elements due to excessive light); (3) insufficient coverage of light to fill shadows; and (4) image shiny, near vertical objects, such as leads.

For example, fixed angle single light sources cannot provide lighting to shadowed areas (such as shorter components surrounded by taller components or areas under vertical leads perpendicular to the scan direction). In order to get the light intensity required for inspection, these fixed angle light sources can also cause "blooming" or very bright spots in the camera (due to the angle of reflection) that prevent inspection of that area because nothing could be discerned from the blooming area. In addition, because solder fillets are "mound-shaped", regardless of the light angle variation, some reflection in a specular fashion back to the camera will occur. To a line scan camera, the shadow areas often look black while the shiny or blooming areas look white and accurate detection of defects in these areas is difficult or impossible.

SUMMARY OF THE INVENTION

The present invention provides a light array illumination system that substantially eliminates or reduces disadvantages and problems associated with previously developed illumination systems and methods used for automated inspections.

More specifically, the present invention provides a system for illumination from a variety of illumination angles to aid inspection of a product. The illumination system includes a dome light array formed in the shape of a partial cylinder about an imaging axis. The dome light array includes a plurality of rows where each row includes a plurality of lamps arranged in an arc about an imaging axis (so that each lamp in the row is approximately the same distance from the imaging axis) and all of the lamps in a row point to and illuminate the same point within the image area. The illumination system can include an aperture in the top of the dome light array through which a camera can image the image area on the object. Positioning each row of lamps in an arc about the image point provides various illumination angles to give a relatively uniform wide angle, yet intense, illumination to enhance automated PWB defect inspection. To further provide illumination, a pair of side panel light arrays having a plurality of lamps can be attached to the sides of the dome light array so that the side lamps provide further vertical illumination on the image area from a horizontal side plane.

The present invention provides an important technical advantage by dramatically improving the image quality and speed of inspection through the use of illumination geometry that is unavailable from previous lighting systems. For example, imaging and inspection of solder joints/bridges and defects associated with the vertical edge of package leads can be greatly enhanced using the lighting system of the present invention. The present invention also allows more reliable inspection of small components located between taller components.

The present invention provides another technical advantage by providing direct specular distribution of light over a large range of angles to reduce flare and shadowing, while maintaining light intensity levels required for imaging with a line scan camera.

The present invention provides yet another technical advantage by reducing the error rate (or number of false defects) during component inspections. For example, by limiting the blooming or glare effect between leads, the present invention can reduce the number of false bridge defects induced by light glare.

Other technical advantages of the present invention include the extended life of the light source when incorporating long life LEDs, the reduced cost of the light source, and the reduced weight of the light source as compared to conventional lighting systems.

Yet another technical advantage of the present invention as compared to fibre optic based lighting systems is the ability to remotely locate the power source. Furthermore, the electrical cable associated with the present invention does not break as easily and is easier to manipulate than fibre optic cable.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

The present invention provides an illumination system that illuminates an image area simultaneously from a wide variety of angles while at the same time maintaining a high enough light intensity for the inspection camera to take a quality image. The geometry of a dome light array having dual side panel light arrays combined with high power LED light sources provides the variety of illumination angles and required light intensity to improve the image quality, reliability and speed of camera-based inspections. The illumination system of the present invention is particularly well suited for illumination of single dimensional subjects automatically inspected using a line scan camera.

By placing an array of light sources on a circumference and pointing each light sources toward the center of the circumference (the "imaging area"), the distance to the imaging area from each light element of the array is the same as every other light element in the array. The fixed distance from each light element to the imaging area is the radius of the circumference. This creates a dome of light sources pointing to the imaging area. Combining this dome of light sources with lighting from side panels also having an array of light elements allows the present invention to provide lighting of adequate intensity for inspection, while minimizing blooming or glinting (e.g., from vertical leads in the scan direction and solder fillets) and shadowing (e.g., from both vertical leads that are not aligned in the scan direction and from taller components surrounding shorter components).

Figure 1:
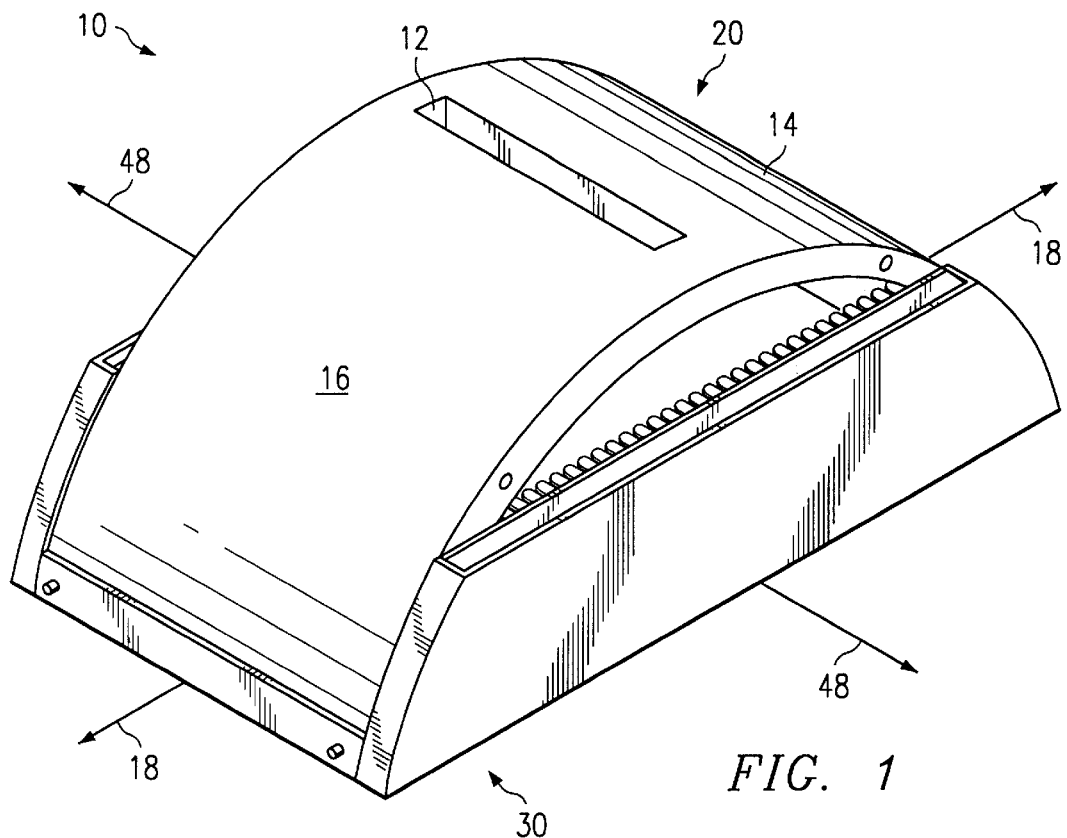
FIG. 1 shows a top perspective view of one embodiment of the illumination system of the present invention.
Figure 2:
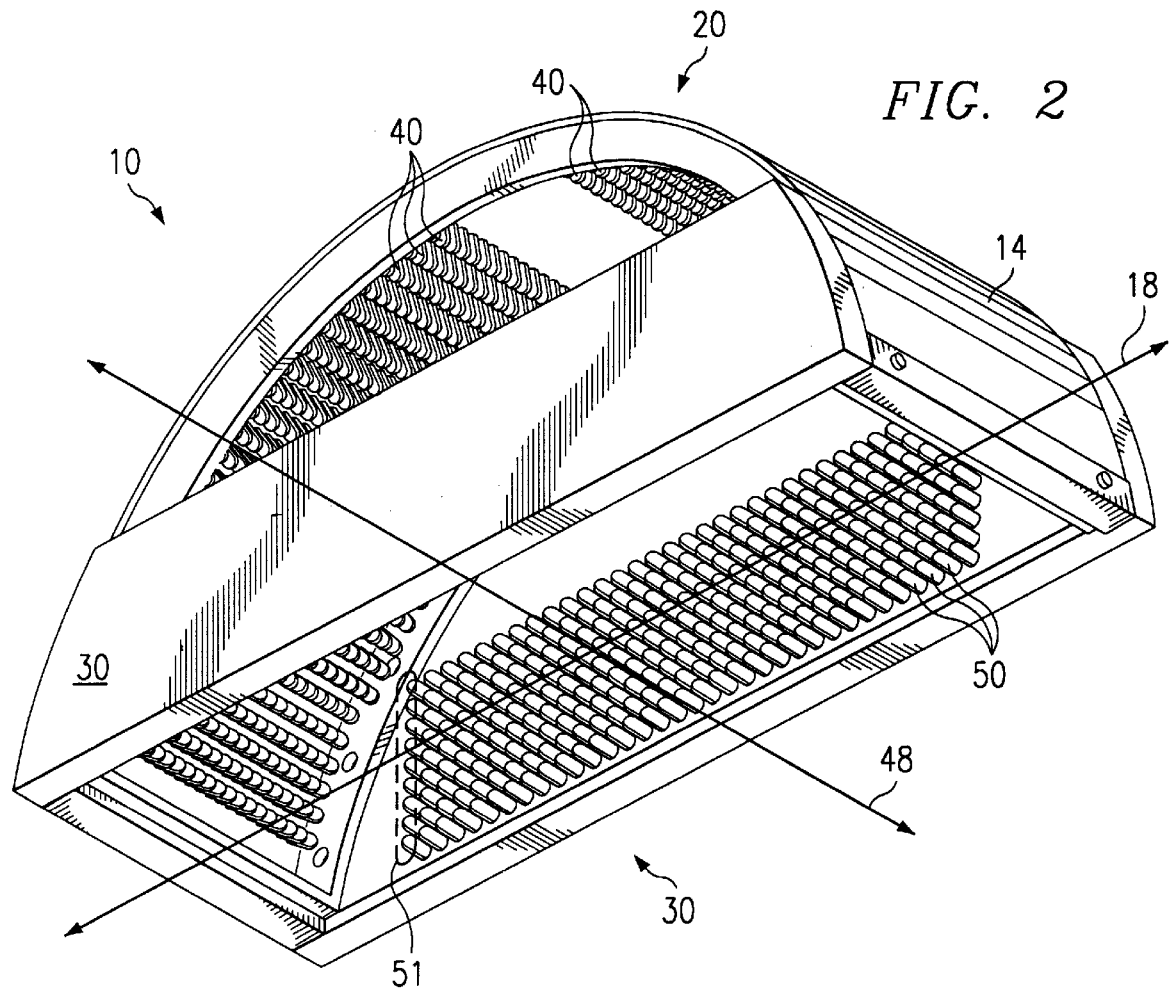
FIG. 2 shows a bottom perspective view of the embodiment of FIG. 1.

FIG. 1 shows a top perspective view of one embodiment of the illumination system 10 of the present invention having a dome light array 20 and a side panel light array 30 coupled to both sides of the dome light array 20. The dome light array 20 includes a dome frame 14 to which a plurality of light sources 40 (as shown in FIG. 2) are attached and a top cover 16. Dome light array 20 also includes aperture 12 through which an inspection camera, such as a line scan camera, can take images of the product such as a PWB to be inspected. Scan axis 18 illustrates the axis that coincides with the scan direction for the embodiment of the illumination system of FIG. 1. Image axis 48 is perpendicular to the scan axis 18 along the image plane 22. The dome frame 14 is formed in the shape of a partial circle, as viewed from either side, where the radius of the circle originates at the image axis. The dome light array 20 thus forms a partial cylinder along and about image axis 48. The width of the aperture 12 and the line imaging device constraints define the imaging width of the image taken. While the present invention will be described herein for the specific application of inspection of PWBs using a line scan camera, it should be understood that the application of the present invention extends beyond that specific application.

FIG. 2 is a bottom perspective view of the FIG. 1 embodiment that shows that shows the plurality of light sources 40 of dome light array 20. Light sources 40 can include light emitting diodes (LEDs), optic lights, and other lighting elements that provide adequate light intensity. As shown, the plurality of light sources 40 can be arranged in rows where each row is an arc along radius R. In the embodiment of FIG. 2, side panel light arrays 30 having a plurality of lamps 50 are attached to each side of dome light array 20 normal to image axis 48. The FIG. 2 embodiment also shows lamps 50 aligned in parallel vertical rows 51. It should be understood that this configuration with approximately parallel rows is optional and other configurations of lamps 50 on side panel light array 30 can be used in conjunction with the present invention.

Figure 3:
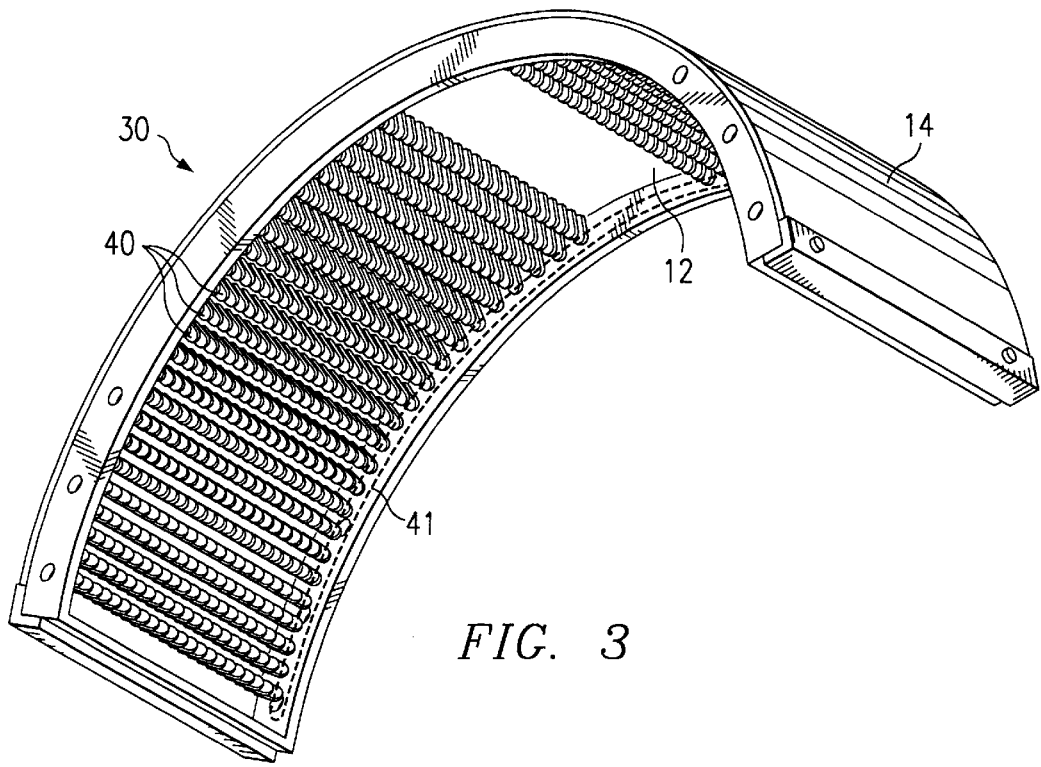
FIG. 3 shows a front end view of an embodiment of the dome light array of the present invention including light sources that are light emitting diodes or LEDs.

FIG. 3 shows a front view of dome frame 14 with light sources 40 attached and aperture 12 cut out from the top of dome frame 14. As shown in the embodiment of FIGS. 2 and 3, the dome light array 20 is a portion of a cylinder about image axis 48, having a radius R where the light sources 40 are positioned so that each light source 40 points approximately to the image axis 48 (i.e., the center point of the cylinder that coincides with the originating point of radius R) which is coincident with (or contained within) the imaging area. The imaging area is the area of the imaging plane that will be imaged by the line scan camera through aperture 12. The imaging area and imaging plane will be described in further detail. The FIG. 3 embodiment shows rows 41 of light sources 40 around the cylinder of dome light array 20. The rows 41 are approximately parallel with each row 41 being one lamp in depth. It should be understood that the spacing within and between rows of light sources, or even whether there are "rows" per say is optional to the specific application.

Pointing each light source 40 at approximately the originating point of the radius (i.e., the center of the circle as viewed from the side or the cylinder of the dome light array 40) assures that each light source 40 contributes to the overall lighting scheme. If each light source 40 has the same intensity, then each light source 40 would then contribute equally to the illumination of the imaging area.

During inspection, a PWB will be placed underneath the dome light array 20 so that the light from the multiple light sources 40 will illuminate an imaging area on the PWB (this imaging area will be coincident with the radius R originating point). Furthermore, the light from the lamps 50 in side panel light arrays 30 will also provide additional illumination on and/or around the PWB imaging area. A line scan camera will take a photograph of the imaging area on the PWB through aperture 12. Either the PWB or camera will then be moved relative to one another so that a different area on the PWB is now within the imaging area and another picture will be taken. This is repeated until the areas of interest on the PWB have all been photographed for inspection.

Figure 5:
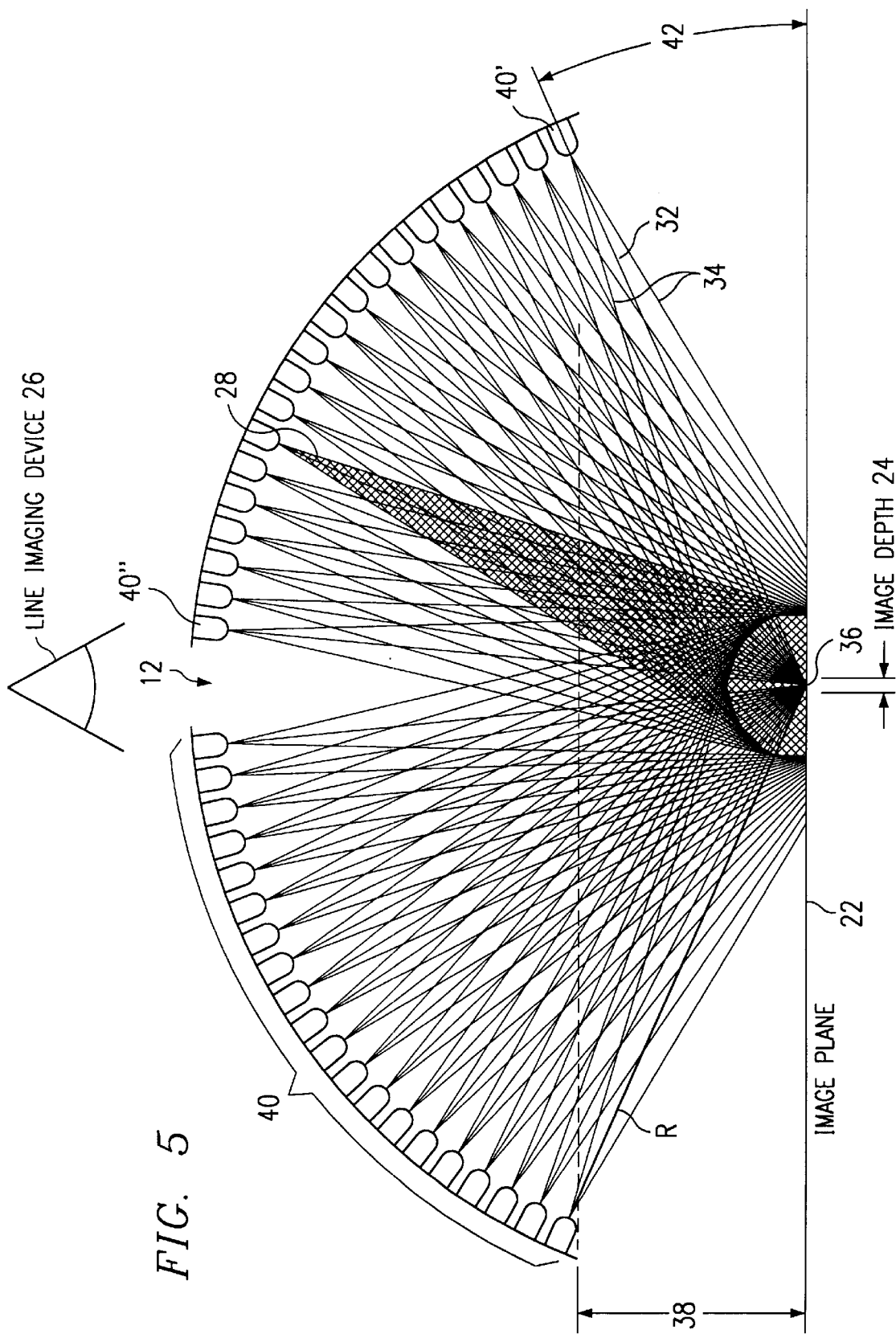
FIG. 5 is a one dimensional representation of the light produced by each light source LED in one row of LEDs of the dome light array and illustrates the cumulative light effect at the image area.

FIG. 5 is a one-dimensional, side view representation of one section of the dome light array 20 as viewed along the image axis that shows a profile of the cumulative light effect of the light sources 40 on the image area 60. Line imaging device 26 takes an image of an object on the image plane 22, where the image has an image depth 24 as defined by the line imaging device 26 and the particular application. As shown in FIG. 5, each light sources 40 is shown with a central ray 32 and outer rays 34 that define the light source's angle of illumination. This angle of illumination defined by the cone of outer rays 34 can vary depending on the type and number of light sources 40 used (i.e., depending on the spacing between light sources 40). As can be seen, the distance between each light source 40 and image point 36 along central ray 32 is defined by radius R. Each light source 40 directly illuminates the image area 60. The clearance 38 shows the distance from the bottom of the dome light array 20 to the image plane 22. Clearance distance 38 should preferably be minimized and is a function of the height of components rising from the imaged object above the image plane. For example, in an automated PWB inspection system using a line scan camera, the PWB board will typically define the image plane 22 while the components will rise above the image plane 22 to certain heights. As the PWB is moved from position to position in order to image all required areas on the PWB, the clearance distance 38 must be sufficient to allow the PWB or camera to be moved on the image plane 22 without causing interference between the illumination system 10 and the components on the PWB. Angle 42 represents the lowest angle of illumination available and is a function of the radius R and the clearance distance 38.

Figure 6:
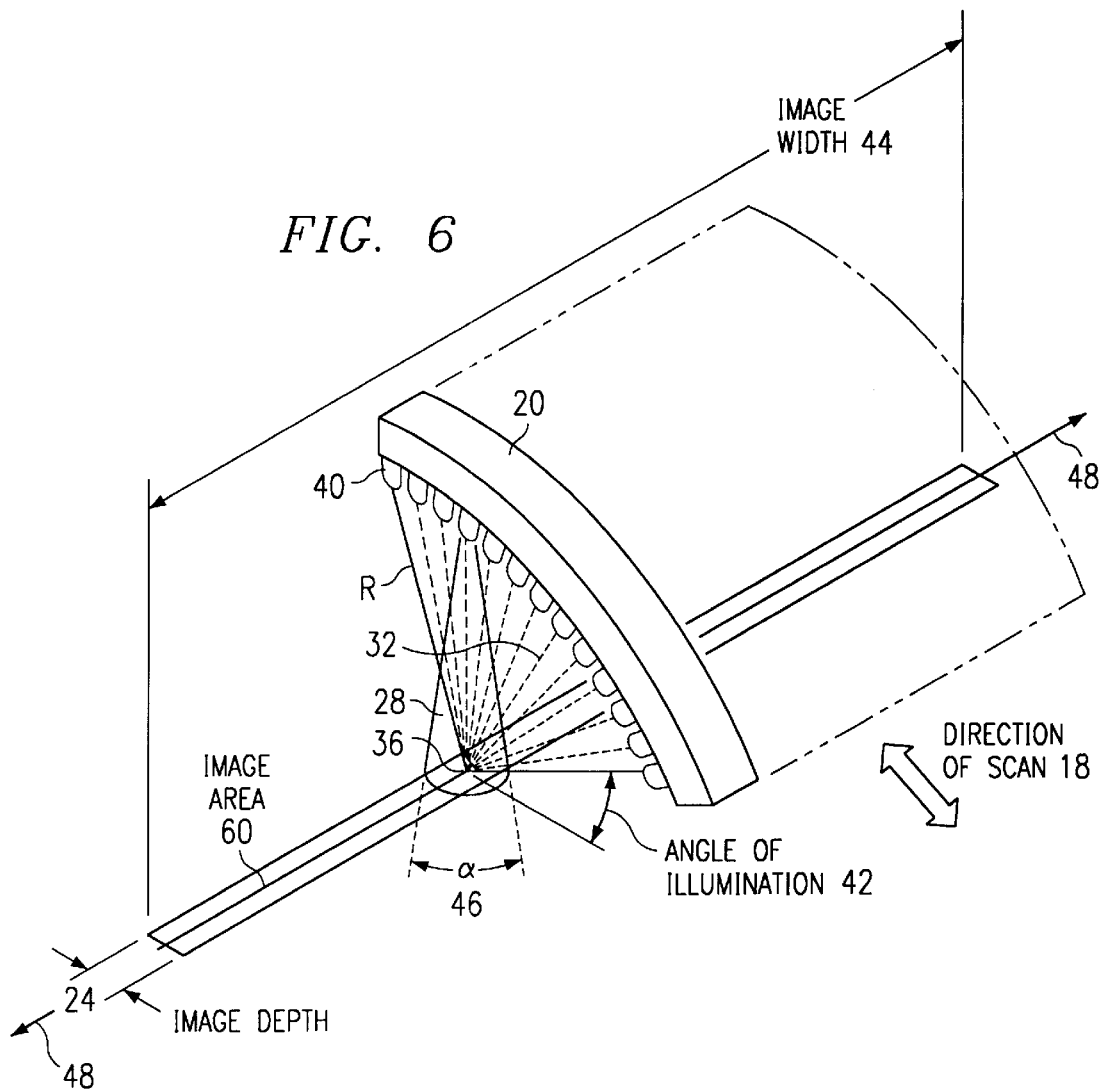
FIG. 6 shows a partial section of a one lamp-depth row of the dome light array of FIG. 2.

FIG. 6 further illustrates the illumination from wide angles from the dome light array 20 on the image area 60. The dome light array section shown in FIG. 6 shows one row of arcs of light sources 40. Each row of light sources 40 along the arc defined by radius R provides illumination 28 onto image area 60 (defined as the image width 44 by the image depth 24) having illumination area 46. The PWB or camera moves along the direction of scan along the scan axis 18. Each light source 40 is positioned at an angle of illumination 42 such that its central ray 32 is approximately pointed at the image point 36. The illumination 28 provides a circle or ellipse of light on the PWB that encompasses a portion of the image area 60.

As shown in FIGS. 5 and 6, each light source 40 in a particular row is positioned such that its central ray 32 is approximately directed to a single image point 36 and further such that each light source in that row is equidistant (approximately radius R) from image point 36. Image plane 22 is the horizontal plane of the PWB that is positioned such that the image point 36, image axis 48, and scan axis 18 are contained on the image plane 22. The image area 60 on the PWB encompasses the image depth 24 and the image width 44 on image plane 22. Each light source 40 has a light contribution 28 (represented by the hatched area for one light source 40 in FIG. 5) that extends beyond the image depth 24. While the central rays 32 from each light source 40 point to approximately the center of the image area 60, the overall illumination from each light source 40 overfills the image area 60. In other words, each lamp has an illumination contribution 28 that covers more than the image depth 24. The most intense light from each light source 40 is at the image point 36 and the light intensity falls off progressively at distances further away from the image point 36 along the image plane 22. The intensity provided by the use of a multitude of light sources 40 results in a greater light intensity so that the central ray 32 of each light source 40 does not have to be precisely aligned to the image point 36. The overfill of these many light sources will average and results an illumination that approximates a uniform illumination from a single light source. Furthermore, the image width 44 can also be overfilled to provide uniform illumination throughout the entire image area 60. At a minimum, the width of the illumination from the light sources must meet the width of the field of view width of interest (as defined by the camera used). For imaging using a line scan camera, an overfill of approximately one inch on either side of the image depth 24 and either side of the image width 44 is more than adequate to provide the light uniformity necessary for automated inspections of PWBs.

FIG. 5 further illustrates that the dome light array 20 of the present invention provides illumination from a variety of angles. Light source 40' provides illumination from a very low illumination angle 42, while light source 40" provides illumination from a very high illumination angle 42. The remaining light sources 50 provide illumination from varying angles between the angle of light source 40' and the angle of light source 40". The low angle illumination allows for improved inspection of vertical leads in the scan axis 18. Narrow angle illumination causes glinting where the percentage of the light that is glinting is relatively high. The wide angle illumination provided by the present invention distributes the light that would potentially cause glinting over a wider angle to reduce the percentage of actual light that is glinting. While wide angle illumination still invites glinting from all of the angles, the energy from each of those glints is greatly reduced to lessen the occurrence of saturation in digital camera cells.

Illumination system 10 can be extended along image axis 48 to accommodate different image widths 44. The radius R may be changed to allow for varying standoff from the imaging area. By increasing the radius R, the light sources 40 within illumination system 10 can be located further away from the image plane 22, and still maintain the low angle illumination properties. As the radius R increases, the area of the light array increases, allowing for more light sources 40 to be incorporated into the dome light array 20. Typically, the intensity of a given light source 40 falls off as the square of the distance. However, by using light sources 40 with integral lenses, and specific angles of illuminations, the working radius R can be extended over a large range. Because each light source 40 on the circumference is directed to the same point on the image area 60, and because light from adjacent light sources 40 overlaps along the axis, the intensity of light tends to average and become uniform.

Figure 8A:
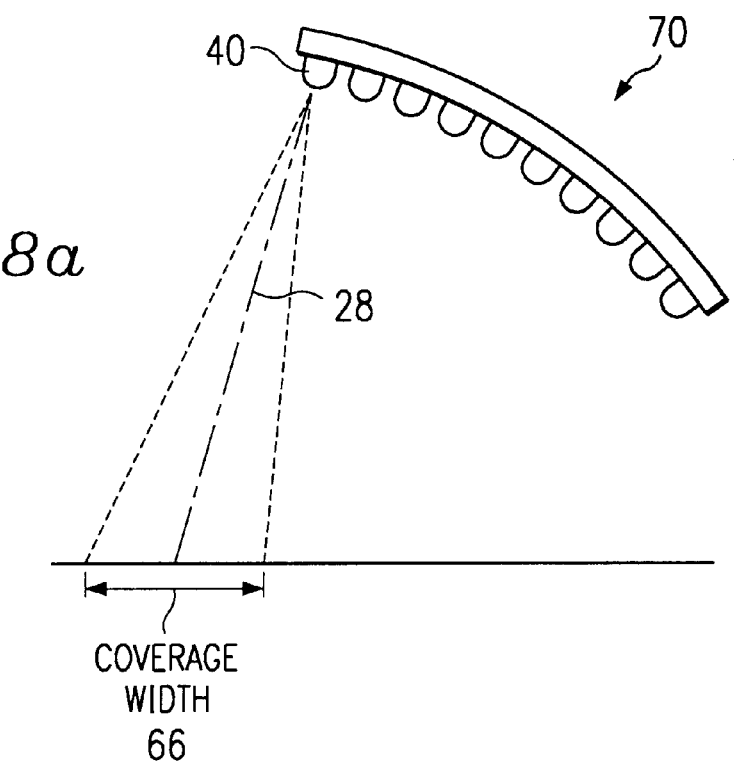
FIGS. 8A and 8B illustrate the difference in lamp and/or light source illumination with and without an optical lens to show the concentration of light using an optical lens.
Figure 8B:
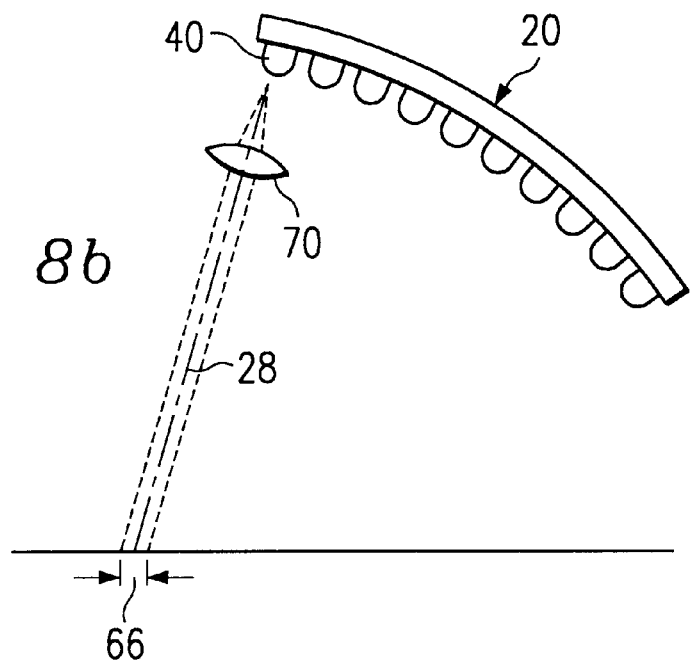

Improvement in uniformity and intensity of light in the image area 60 can be achieved by incorporating a short focal length cylindrical lens 70 in conjunction with each light source 40. The diverging beam can be collimated or focused over the depth of the image area 60, while the same smoothing caused by overlapping beams will still make the line of light intensity uniform and smooth. FIGS. 8A and 8B illustrate the differences in these types of light sources. In FIG. 8A, the light source 40 provides a diverging illumination area 28 that has a coverage width 66. By adding a cylindrical imaging optic 70 to a point source (e.g., a small filament or LED chip), the light is focused along one dimension and allowed to diverge along the other. When pointed at a flat surface normal to the light source 40 and lens 70, a line of light would be presented. By rotating the light source 40 and lens 70 about its cylindrical axis and adjusting the angular parameters, the line of light can be directed to coincide with the image area 60 with a coverage width 66 that is greatly contracted. This results in less wasted light. Adjusting the position of the line of light on the image area 60 can help create a more uniform illumination field along the length of the image area 60. Methods of generating the line of light can include separate cylindrical optics 70 on each light source 40, or alternatively, molding a cylindrical optic 70 into the light source itself (LEDs are a likely candidate) or creating an array of cylindrical lenses 70 in a mask that would be used to hold the light sources 40 at the correct angles and cast the line of light at the subject.

The requirements for a quality image exist along the image axis 48 as they do along the scan direction or scan axis 18 (i.e., lighting of adequate intensity and from as full a range of angles as possible). While the dome light array 20 provides excellent uniform lighting from a broad range of angles along the scan axis 18 of the imaged area, adequate illumination from the end of the image area 60 (along image axis 48) to eliminate shadowing may require additional illumination. The side panel light arrays 30 can provide this type of illumination for leads and other components along the image axis 48.

Three alternative embodiments of side panel light arrays 30 are provided for illumination along the image axis 48. As intensity requirements increase, due to the width of the image area 60 or sensitivity issues with the camera, the complexity of the illumination panel may be increased to improve efficiency. For each embodiment described and shown in FIGS. 4 and 7, the side panel light array 30 has a plurality of lamps 50 where the lamps 50 are aligned in approximately parallel rows 51. The illumination system 10 can include a side panel light array 30 attaches to both sides of the dome light array 20 to provide lighting along the image axis 48 from both sides toward the interior of the illumination system 10.

The lamps 50 can include LEDs, and particularly can include diffuse LEDs. Diffuse LEDs have a frosted appearance, essentially making the surface of the lamp 50 a light emitter, making the lamp 50 appear larger. The illumination cast by such a lamp 50 is distributed over a large angle, so that even if the lamp 50 is not directly pointed at the image area 60, some light from the lamp 50 will fall on the region of interest. Other types of lighting elements can also be used for lamps 50.

Figure 4:
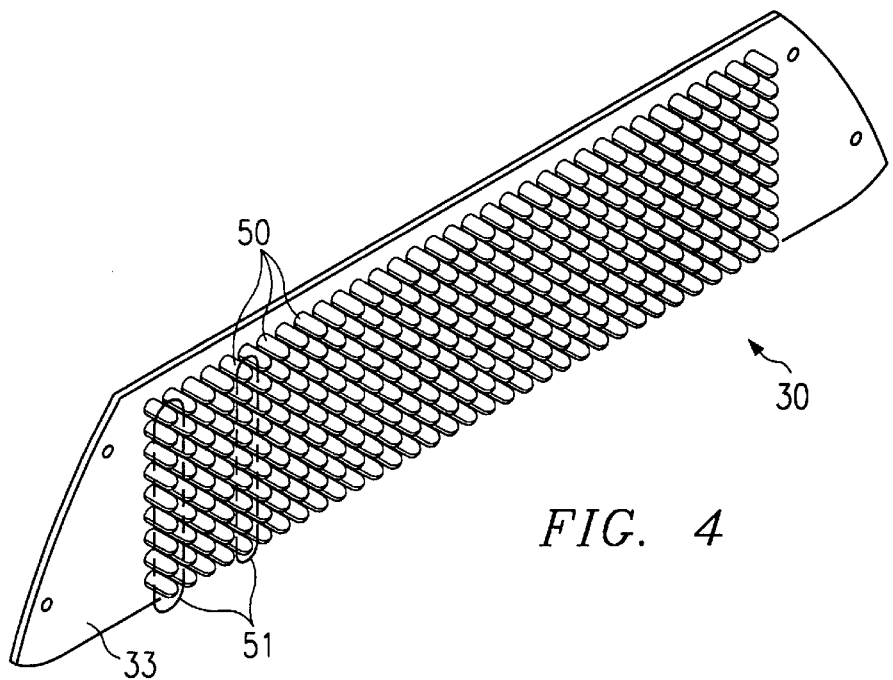
FIG. 4 is an embodiment of a side panel light array of the present invention including lamps that are LEDs.

For the embodiment of FIG. 4, the lamps 50 are positioned such that the central light ray from each LED 50 shines approximately perpendicular to the side panel frame 33 (i.e., at a ninety degree angle from side panel light array 30). Thus, if the side panel light array 30 is mounted at a right angle to the dome frame 14 on each side of dome light array 20 (as shown in FIGS. 1 and 2), then the lamps 50 from each side panel light array 30 are pointed at one another along the image axis 48. Using this embodiment of the side panel light array 30 with intense, diffuse lamps 50 will result in a very broad light source that floods the interior, and thus the image area 60, with light from an extended range of angles. By using a large number of diffuse lamps 50, enough intensity can be generated to provide adequate fill light along the image axis 48. Even if no lamp 50 is directly pointed at the image area, some light from each lamp 50 will fall on the region of interest. While most of the optical energy is not incident on the image area 60, the light that does fall on the image area 60 is reasonably uniform and even. The side panel light array 30 of FIG. 4 provides approximately uniform illumination over a vertical area from a two-dimensional horizontal surface. The side panel light array 30 embodiment of FIG. 4 could also be attached to the side of the dome light array 20 at an angle such that the light from the lamps 50 points downward toward the image plane 22.

Figure 7:
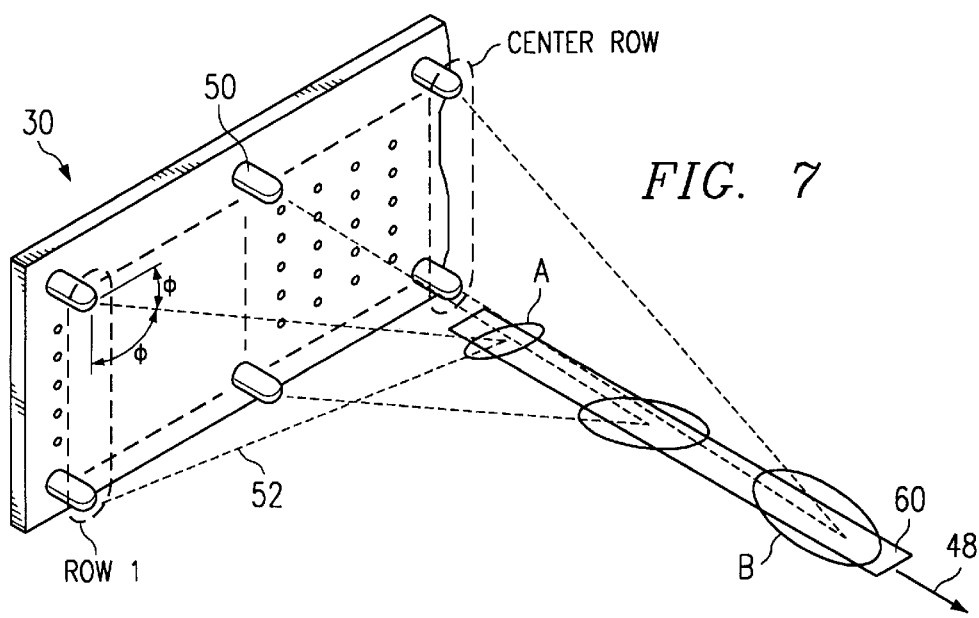
FIG. 7 illustrates another embodiment of the side panel light array having a different lamp directional arrangement.

In cases where simple diffuse LED lamps do not provide adequate energy, a focused side panel light array 30 can be constructed to illuminate along the image axis 48. This type of side panel light array 30 can use LEDs 50 having clear lenses and where each vertical row of lamps 50 is rotated to throw light over an angle determined by the field of view to be covered and the number of light elements in the array. FIG. 7 shows a partial view of a side panel light array 30 with focused image axis illumination. As shown, each lamp 50 within a vertical row of lamps 50 is rotated (as compared to the position in FIG. 4) and positioned so that the central optical ray 52 from each lamp 50 in a particular vertical row is directed at a specific point within the image area 60. Thus, each section within the image area 60 on the PWB would be illuminated by a series of lamps 50, but from different angles. For example, the lamps 50 in the vertical row labeled row 1 would illuminate the section of the image area 60 labeled Area A. Though only the upper and lower lamps 50 are shown, it should be understood that other lamps 50 can be contained in row 1 between these two lamps. Each lamp 50 in row 1 would be positioned within side panel light array 30 so that the central ray 52 would illuminate approximately the center of Area A within image area 60. As shown, this allows illumination of the portion of Area A on image area 60 from a variety of illumination angles. Thus, the more lamps 50 on the side panel light array 30, the greater number of illumination angles. As shown in FIG. 7, each row of lamps 50 can be positioned to equalize, as much as possible, the distance the light from each lamp 50 must travel to each point along the image area 60 width. Equalizing the distance the light from each lamp 50 travels provides more uniform lighting.

For example, as shown, Row 1 of lamps 50 illuminate the portion of the image area 60 that is closest to side panel light array (i.e., area A), while the row of lamps 50 labeled "Center Row" are set to cast their light at the far end of the image area (labeled Area B). As the distance from the end of the imaging area 60 to the lamps 50 increases, the lamps 50 would cast their illumination progressively closer to the end of the image area 60 nearest the side panel light array 30. By doing this, the present invention reduces lighting unevenness caused by the expanding properties of light caused by the fact that the intensity of light falls off as function (typically square) of the distance from the light to the subject. By positioning the lamps with appropriate angles of illumination, less light will fall on non-image areas, increasing the intensity on the image area 60. This could be accomplished with a side panel light array 30 having fixed lamps located in holes that would have a unique pointing direction definable by two angles—the downward angle $\phi$ which defines how far from perpendicular toward the image plane the central ray will point and the inward angle $\theta$ which defines how far from perpendicular toward the center of the side panel light array 30 the central ray 52 will point.

Yet another embodiment of the side panel light array 30 would incorporate the focused array concept with the lamp 50 as described in FIG. 7, but would additionally include the cylindrical imaging optics 70 of FIG. 8B on each lamp element 50. This provides the advantages of both a focused direction and a reduced illumination width. Thus, instead of focusing a row of lamps 50 at the same image point 36, each lamp 50 can be pointed at a different image point 36 to form a line of light across the image depth 24. By aiming each adjacent lamp 50 in a vertical row to an adjacent image point on the image area, the entire image area 60 can be covered by a single row of lamps 50. By having each row of lamps 50 covering the entire image area 60, the image area is illuminated from the side panel light array 30 from a multitude of angles.

Liquid cooling of the light sources 40 and lamps 50 can be used to help maintain long working life at elevated light output levels. Alternatively, a fan could be incorporated within the dome light array 20 to force air from the area above the image plane out through a vent. The fan and vent could also address the problem of heat shimmering that can cause optical distortion. A PWB can be hot when it enters the automated inspection system. Hot air has a different density and different optical property than room temperature air and can cause optical distortion. Using a fan in conjunction vents cut into the cover 16 of the dome light array 20 can allow the hot air to be vented away from the optical path of the line scan camera. For some cameras, peak light intensity can be increased up to 10 times using duty cycle constrained impulse drivers.

The illumination system 10 of the present invention will work with a very diverse set of lighting elements, including incandescent, fiber optic, and LED light sources and lamps. It should be understood that advances in LED and other light sources are anticipated that will result in increased light output, use of color inspections with white light LEDs, and increased array density. It should be understood that while the light sources 40 and lamps 50 have been described separately and identified with different reference numerals, these could be the same type of LED or lighting element. The light sources 40 and lamps 50 can include light emitting diodes having a wide range of light intensities.

The light sources 40 and lamps 50 are supplied electrical current to power these lighting elements. For the specific embodiments described herein, individual LEDs have been wired in series in banks of 11, with those banks wired in parallel. Each LED used for these specific embodiments requires a forward voltage slightly lower than 2 volts. By wiring 11 lamps in series we are able to power the array with commonly available power supplies capable of providing 20 volts DC. For fine control, a computer feedback systems provides an analog reference to the power supply, which tunes the voltage to the lamp, which in turn causes the current level to change, altering light level, as shown in more detail in FIGS. 9 and 10.

When LEDs used are used as light sources 40 and lamps 50, they can have varying intensities. Any light source/lamp capable of maintaining the minimum energy density required under the inspection operating conditions (such as the camera requirements, scan rate, PWB configuration, inspection criteria, etc.) can be used in the present invention. Because the LEDs have differhng intensities and illumination angles, a proper means of comparison is optical energy density at the plane of illumination, or image plane. Energy density is defined by the following equation:

$$\text{energy density} = \frac{\text{rating}}{\text{spotsize}} \ (\text{mcd}/\text{in}^2)$$

where rating is the millicandle rating of the LED and spotsize is the area the LED will illuminate on the illumination plane.

For the present invention, it is the energy density at the image plane 22, rather than the intensity of the particular light source 40 and/or lamp 50 that is important. Changes in the radius R will result in changing energy density at the image plane 22. As the radius R that defines the distance between the light element and the image plane 22 increases, the energy density will decrease if the LED intensity and illumination angle remain fixed. The lower bound of energy density for any radius R will be determined by the operating conditions such as camera sensitivity and scan rate. The upper bound of energy density for any radius R is limited only by the light element parameters, including number, intensity and illumination angle. Specific energy densities can be maintained when the radius R of the dome frame 14 changes, so long as the LED light intensity and illumination angles can be adjusted to compensate for the increased radius. Typically, energy density will proportionally decrease as the square of the distance change away from the subject image plane. The constant of proportionality is the illumination angle (angular spread that contains light above 50% of the maximum value). Thus, the radius R can be increased in conjunction with an illumination angle decrease in order to maintain a specific range of energy density. Alternatively, the LED intensity can be increased proportionally to compensate for an increase in the fixture radius R. These two parameters could also be adjusted in combination to maintain a specific energy density.

Lighting characteristics were determined for an embodiment of the illumination system 10 in which the dome light array 10 has a depth of approximately 9.5 inches, a width of approximately 6.5 inches, and an height of approximately 4 inches. The radius R was approximately 4.25 inches with the plurality of light sources 40 mounted at the 4.25 inch location. The dome light array 20 contained 23 arc rows 41, each containing 22 light sources 40 on either side of aperture 12 (for a total of 1012). The 1012 light sources 40 were Kingbright L1513SRC/E light emitting diodes or LEDs having an illumination angle of twenty degrees and a light intensity of approximately 3500 millicandles. The aperture was approximately 0.5 inches in depth and 5.5 inches in width. The side panel light arrays 30 have a depth of approximately 9.5 inches and a height of approximately 2 inches. Each side panel light array 30 included 9 rows and 33 columns of lamps 50 (for a total of 594 lamps 50). The lamps 50 used were Kingbright L53SRD/G diffuse LEDs having sixty degree illumination angles and approximately 1000 millicandle light intensity. Both the lamps and the light sources were single wavelength red light LEDs (used because a line scan camera used is sensitive to red light). This embodiment of the illumination system 10 produced 800 foot candles at the radius. Additional results of the testing of this unit are shown in FIGS. 9–11.

Figure 9:
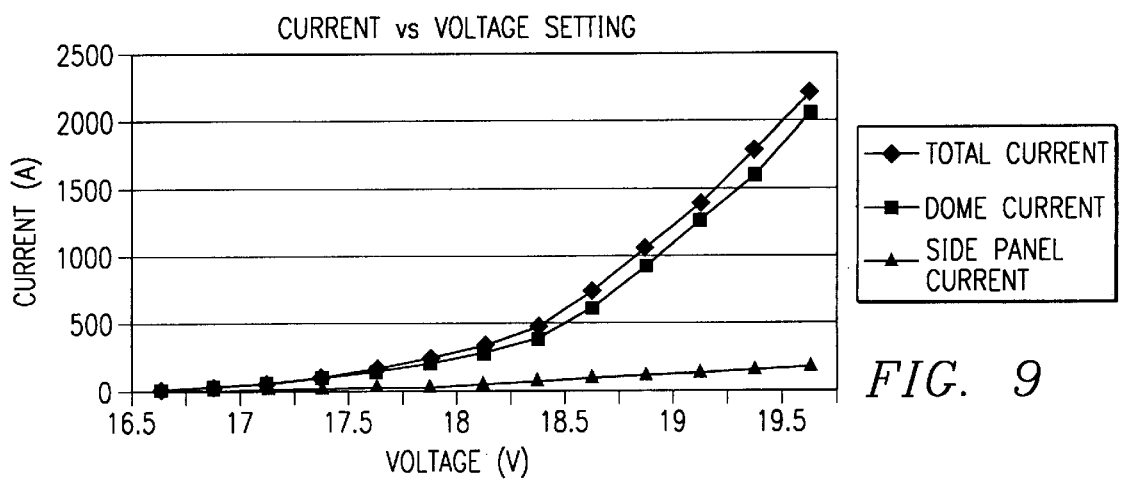
FIG. 9 is a graph of current versus voltage for a particular embodiment of the present invention.

FIG. 9 shows a graph of current used to drive the illumination system 10 versus the voltage. The graph breaks out the current used by the dome light array 20 and the side panel light arrays 30, respectively, when driven at the same voltage. As FIG. 9 shows, the side panel light arrays 30 conduct less current than the dome light array 20 by a considerable margin. This test shows that the voltage to the side panel light arrays 30 can be increased while the voltage to the dome light array 20 can be reduced in order to balance the lighting at the image area 60.

Figure 10:
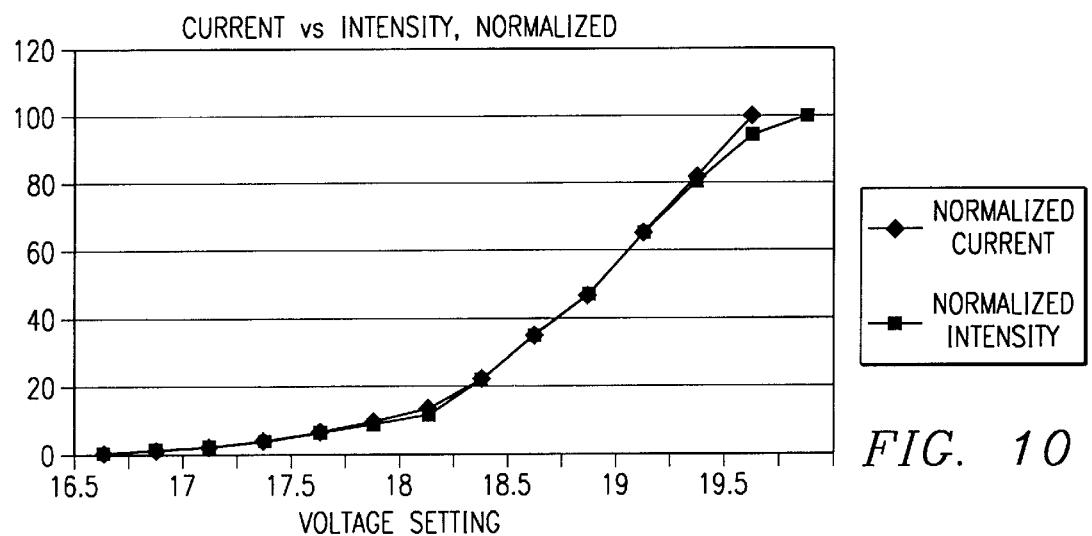
FIG. 10 is a graph showing the relationship between current and light intensity on a normalized basis for a particular embodiment of the present invention.

FIG. 10 shows the relationship between the current drawn by the dome light array 20 and the light intensity at the image area on a normalized basis. It is clear that for this embodiment of the invention, the light intensity follows current with little deviation. This allows an inference of intensity from current readings.

Figure 11:
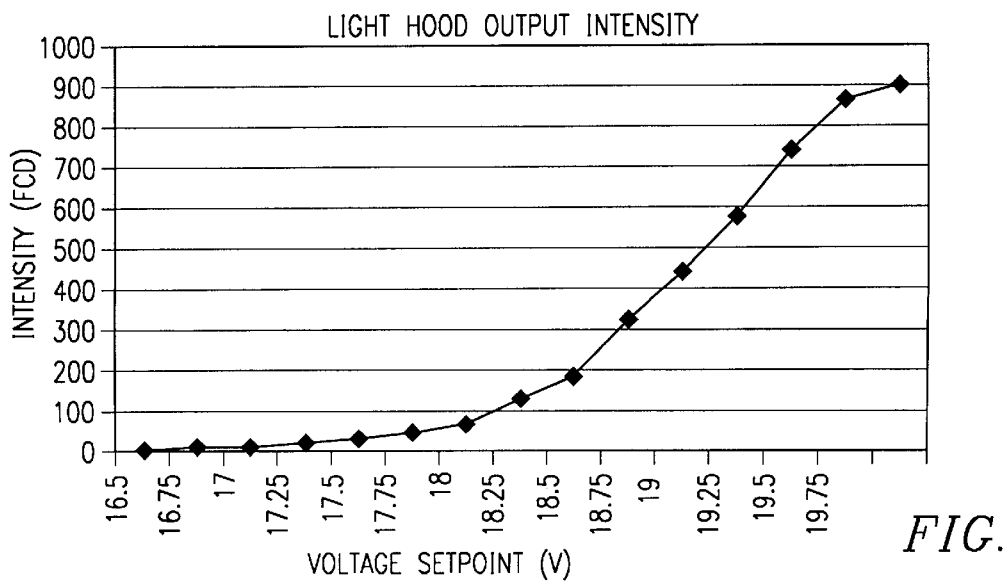
FIG. 11 is a graph of the relationship between current and light intensity for a particular embodiment of the present invention.

FIG. 11 shows the light output in foot candles as a function of voltage for the dome light array 20. The light intensity readings were taken with a light meter placed at the radius of the light source. This provides a useful tool in comparing the light intensity of the present invention with other light sources.

Although the present invention has been described in detail, it should be understood that various changes, substitutions and alterations can be made hereto without departing from the spirit and scope of the invention as described by the appended claims.

What is claimed is:

1. An illumination system capable of providing wide angle illumination to an image area on an image plane within an interior of the illumination system, comprising:
   a dome frame having a cylindrical geometry defined by a radius beginning at an image axis on the image plane so as to form a partial cylinder about the image axis;
   a plurality of light sources coupled to the dome frame so that each light source is approximately the same distance from the image axis, the plurality of light sources positioned such that a central ray of light from each light source strikes approximately the image axis within the image area; and
   a side panel light array coupled to the dome light array, comprising:
      a pair of side panel frames coupled to the dome frame; and
      a plurality of lamps coupled to each side panel frame and positioned so as to provide illumination within the interior of the illumination system.

2. The system of claim 1 wherein the plurality of light sources illuminates an illumination area having an image depth about the image axis.

3. The system of claim 1, wherein the plurality of lamps in each side panel light array is arranged in a plurality of vertical rows, and wherein each lamp is positioned such that a lamp central ray from each lamp strikes approximately an image point within the image area.

4. The system of claim 3, wherein each lamp within a single vertical row of lamps is positioned such that all central rays from each lamp in each vertical row of lamps strikes the same image point, and further wherein each lamp is positioned so that the distance each lamp central ray travels is approximately equal.

5. The system of claim 3, further comprising a cylindrical image optics positioned between the each lamp and the image area, and wherein the cylindrical image optics works in conjunction with each lamp so that the light cast by each lamp is a line of light through the entire image depth.

6. The system of claim 1, further comprising a cylindrical lens image optic positioned between each light source and the image area to provide more focused illumination at the image area from each light source.

7. The system of claim 1, wherein each light source is a light emitting diode having an intensity ranging from 200 to 5000 millicandles and each lamp is a light emitting diode having an intensity ranging from 200 to 5000 millicandles.

8. The system of claim 1, wherein the plurality of light sources provides a cumulative light contribution that overfills the image area.

9. The system of claim 1, further comprising:
   a fan; and
   a vent cut out of a top cover of the dome light array, wherein the fan and vent coordinate to direct air away from a space between the aperture and the image area.

10. An illumination system capable of providing wide angle illumination to an image area on an image plane within an interior of the illumination system, comprising:
    a dome light array, comprising:
       a cylindrical dome frame having a geometry defined by a radius beginning at an image axis on the image plane so as to form a partial circle as viewed along the image axis;
       a plurality of light sources coupled to the dome frame so that each light source is approximately the same distance from the image axis, the plurality of light sources positioned such that a central ray of light from each light source points towards the image axis within the image area to illuminate an illuminate area that has an image depth about the image axis; and
       an aperture in the dome frame; and
    a side panel light array coupled to the dome light array, comprising:
       a pair of side panel frame coupled to the dome frame; and
       a plurality of lamps coupled to each side panel frame and positioned so at to provide illumination within the interior of the illumination system.

11. The system of claim 10, wherein the plurality of lamps in each side panel light array is arranged in a plurality of vertical rows, and wherein each lamp is positioned such that a lamp central ray from each lamp strikes approximately an image point within the image area.

12. The system of claim 11, wherein each lamp within a single vertical row of lamps is positioned such that all central rays from each lamp in each vertical row of lamps strikes the same image point, and further wherein each lamp is positioned so that the distance each lamp central ray travels is approximately equal.

13. The system of claim 11, further comprising a cylindrical image optics positioned between the each lamp and the image area, and wherein the cylindrical image optics works in conjunction with each lamp so that the light cast by each lamp is a line of light through the entire image depth.

14. The system of claim 10, further comprising a cylindrical lens image optic positioned between each light source and the image area to provide more focused illumination at the image area from each light source.

15. The system of claim 10, wherein the plurality of light sources provides a cumulative light contribution that overfills the image area.

16. The system of claim 10, wherein the dome light array is positioned above the image plane at a clearance distance sufficient to prevent interference with a component an object being inspected during inspection.

17. The system of claim 10, further comprising:
    a fan; and
    a vent cut out of a top cover of the dome light array, wherein the fan and vent coordinate to direct air away from a space between the aperture and the image area.

18. An illumination system for use in automated inspection of an image area on an image plane, comprising:
    a dome light array, comprising:
       a dome frame having a first side and a second side distal the first side, wherein the geometry of each side is a circle about an image axis defined by a radius beginning at the image axis on the image plane, the dome frame forming a partial cylinder about the image axis;
       a plurality of light source rows, each light source row comprising a plurality of light sources coupled to the dome frame on an interior of the dome frame, the plurality of light sources positioned such that a central ray of light from each of light sources strikes approximately an image point on the image axis, and wherein each light within in a single row strikes the same imaging point on the image axis; and an aperture in the dome frame through which the line scan camera can take an image of the PWB; and a first side panel light array, comprising:
a first side panel frame coupled to the first side of the dome frame; and
a plurality of first side panel light array lamps coupled to the side panel frame and positioned so at to provide illumination within the interior of the illumination system; and a second side panel light array, comprising:
a second side panel frame coupled to the second side of the dome frame; and
a plurality of second side panel light array lamps coupled to the side panel frame and positioned so at to provide illumination within an interior of the illumination system.

19. The system of claim 18, wherein the first and second side panel frames are mounted to the dome frame at approximately a ninety degree angle to the image plane, and wherein the each of the lamps is positioned on its respective side panel frame such that a lamp central ray from each lamp shines at approximately a ninety degree angle to the side panel frame to which it is coupled.

20. The system of claim 18, wherein the plurality of lamps in each side panel light array is arranged in a plurality of vertical rows, and wherein each lamp is positioned such that a lamp central ray from each lamp strikes approximately an image point within the image area.

21. The system of claim 20, wherein each lamp within a single vertical row of lamps is positioned such that all central rays from each lamp in each vertical row of lamps strikes the same image point, and further wherein each lamp is positioned so that the distance each lamp central ray travels is approximately equal.

22. The system of claim 20, further comprising a cylindrical image optics positioned between the each lamp and the image area, and wherein the cylindrical image optics works in conjunction with each lamp so that the light cast by each lamp is a line of light through the entire image depth.

23. The system of claim 22, wherein the plurality of lamps is positioned such that every image point along the entire image area receives illumination from at least one lamp.

24. The system of claim 18, further comprising an image optic positioned between each light source and the image area to provide more focused illumination at the image area from each light source.

25. The system of claim 24, wherein the image optic is a cylindrical lens.

26. The system of claim 18, wherein each light source is a light emitting diode having an intensity greater than 100 millicandles and each lamp is a light emitting diode having an intensity greater than 100 millicandles.

27. The system of claim 18, wherein the plurality of light sources provides a cumulative light contribution that overfills the image area.

28. The system of claim 20, wherein the plurality of light sources in each light source row exceeds 15 and plurality of lamps in each vertical row exceeds 5.

29. The system of claim 18, wherein an energy density at the image area exceeds 1000 mcd/in$^2$.

30. The system of claim 18, wherein the dome light array is positioned above the image plane at a clearance distance sufficient to prevent interference with a component on the PWB during inspection.

31. The system of claim 18, wherein the light intensity at the image area can be closely approximated based on a current input to the dome light array.

32. The system of claim 18, further comprising:
a fan; and
a vent cut out of a top cover of the dome light array, wherein the fan and vent coordinate to direct air away from a space between the aperture and the image area.

33. A method for illumination of an image area defined by an image width and an image depth wherein an image axis runs through and divides the image depth in equal halves, the image area to be imaged by an imaging device, the method comprising:

illuminating the image area from a plurality of light sources in a plurality of rows, each light source positioned at a radius about the image axis such that each light source is approximately an equal distance from the image axis, wherein each row of light sources is also positioned such that a central light source ray from each light source strikes approximately an image point on the image axis; and illuminating the image area along the image axis from a first plurality of lamps proximate a first end of the image area and from a second plurality of lamps proximate a second end of the image area and distal the first plurality of lamps, and wherein the first plurality of lamps generally faces the second plurality of lamps.

34. The method of claim 33, wherein the plurality of lamps in each side panel light array is arranged in a plurality of vertical rows, and wherein each lamp is positioned such that a lamp central ray from each lamp strikes approximately an image point within the image area.

35. The method of claim 34, wherein each lamp within a single vertical row of lamps is positioned such that all central rays from each lamp in each vertical row of lamps strikes the same image point, and further wherein each lamp is positioned so that the distance each lamp central ray travels is approximately equal.

36. The method of claim 34, further comprising positioning a cylindrical image optics between the each lamp and the image area so that so that a light cast by each lamp is a line of light through the entire image depth.

37. The method of claim 33, further comprising providing a cumulative illumination that overfills the image area.

38. The method claim 33, further comprising directing air within the interior of the illumination system away from a space near the image area.

39. An illumination system for providing illumination to an image area on an image plane, comprising:

a cylindrical frame comprising a series of semicircular sections, wherein each semicircular section is proximate to at least one other semicircular section to provide a partially cylindrical frame about the image axis; and a plurality of light sources coupled to the cylindrical frame so that each light source is approximately the same distance from the image axis, the plurality of light sources positioned such that a central ray of light from each light source strikes approximately the image axis within the image area.

40. The illumination system of claim 39, wherein an illumination area illuminated by the plurality of light sources is a linear illumination area.

* * * * *